United States Patent [19]

Obermeier et al.

[11] Patent Number: 5,663,291
[45] Date of Patent: Sep. 2, 1997

[54] PROCESS FOR OBTAINING INSULIN HAVING CORRECTLY LINKED CYSTINE BRIDGES

[75] Inventors: Rainer Obermeier, Hattersheim; Martin Gerl, Kriftel; Jürgen Ludwig, Brachttal; Walter Sabel, Bad Camberg, all of Germany

[73] Assignee: Hoechst Aktiengesellschaft, Frankfurt am Main, Germany

[21] Appl. No.: 389,487

[22] Filed: Feb. 16, 1995

[30] Foreign Application Priority Data

Feb. 18, 1994 [DE] Germany .................. 44 05 179.4

[51] Int. Cl.⁶ .................. C07K 1/107; C07K 14/00; C12P 27/06
[52] U.S. Cl. .................. 530/303; 435/68.1; 530/305
[58] Field of Search .................. 435/68.1; 530/303, 530/305

[56] References Cited

U.S. PATENT DOCUMENTS

| | | | |
|---|---|---|---|
| 4,616,078 | 10/1986 | Dimarchi | 530/305 |
| 4,877,868 | 10/1989 | Reno et al. | 530/390 |
| 5,231,178 | 7/1993 | Holtz et al. | 530/399 |
| 5,245,008 | 9/1993 | Dickhardt et al. | 530/305 |
| 5,442,043 | 8/1995 | Fukuta et al. | 530/303 |
| 5,473,049 | 12/1995 | Obermeier et al. | 530/303 |
| 5,523,293 | 6/1996 | Jane et al. | 514/21 |

FOREIGN PATENT DOCUMENTS

| | | |
|---|---|---|
| 0037255 B2 | 10/1981 | European Pat. Off. |
| 0037255 A1 | 10/1981 | European Pat. Off. |
| 0055945 A3 | 7/1982 | European Pat. Off. |
| 0219874 B1 | 4/1987 | European Pat. Off. |
| 0347781 B1 | 12/1989 | European Pat. Off. |
| 0379162 A2 | 7/1990 | European Pat. Off. |
| 0453969 A1 | 10/1991 | European Pat. Off. |
| 0600372 A1 | 6/1994 | European Pat. Off. |
| WO 91/03550 | 3/1991 | WIPO |

OTHER PUBLICATIONS

Humbel et al., Biochemistry 7 (2): 621–629, (1968).
R. Jaenicke et al., "Folding Proteins," Protein Structure, A Practical Approach, Ed. T.E. Creighton, IRL Press Oxford (1984) pp. 191–223.
W. Kemmler, et al., J. Biol. Chem. 246: 6786–6791 (1971).
U. K. Laemmli, Nature, 277: 680–685 (1970).
B. H. Frank et al., "The Production of Human Proinsulin and Its Transformation to Human Insulin and C-peptide," Proc. 7th Am. Pept. Symp., (1981) pp. 729–738.
Wetzel, R. "Expression in Escherichia Coli of A Chemically Synthesized Gene For A Mini-C Analog of Human Proinsulin" GENE Bd. 16: 63–71 (1981).
European Search Report dated Dec. 22, 1995.
Slonina, P. et al. "Breakthrough Curves ... Divinylbenzene" Journal of Chromatography 537 (1991) pp. 167–180.
Wang, J. Y. et al. Stability and Characterization ... Drugs Plenum Press, 1993 p. 317.

*Primary Examiner*—Jeffrey E. Russel
*Assistant Examiner*—Kathleen Carroll
*Attorney, Agent, or Firm*—Finnegan, Henderson, Farabow, Garrett & Dunner, L.L.P.

[57] ABSTRACT

A process for obtaining insulin having correctly linked cystine bridges from a corresponding proinsulin amino acid chain in the presence of mercaptan, chaotropic auxiliaries and at a pH of 10 to 11 is described, as well as the direct conversion of the proinsulin to insulin with the aid of enzymes and direct isolation of the insulin from the reaction mixture with the aid of hydrophobic adsorber resins.

18 Claims, No Drawings

PROCESS FOR OBTAINING INSULIN HAVING CORRECTLY LINKED CYSTINE BRIDGES

Human insulin is a protein having two amino acid chains containing altogether 51 amino acid residues. 6 cysteine residues occur in the two amino acid chains, each two cysteine residues being linked to one another via a disulfide bridge. In biologically active human insulin, the A and B chains are linked with one another via two cystine bridges, and a further cystine bridge occurs in the A chain. Looked at statistically, there are 15 possibilities for the formation of disulfide bridges within a human insulin molecule. Only one of the 15 possibilities occurs in biologically active human insulin. The following cysteine residues are linked with one another in human insulin:

A6–A11
A7–B7
A20–B19

The letters A and B stand for the particular insulin amino acid chain, and the number for the position of the amino acid residue, which is counted from the amino to the carboxyl end of the particular amino acid chain. Disulfide bridges can also be formed between two human insulin molecules so that infinitely many different disulfide bridges can easily be formed.

A known process for the preparation of human insulin is based on the use of human proinsulin. Human proinsulin is a protein having a linear amino acid chain of 86 amino acid residues the B and A chains of the human insulin being linked with one another via a C peptide having 35 amino acid residues. The formation of the disulfide bridges occurring in human insulin takes place via an interme-diate, the cysteine residues of the human insulin being provided with a sulfur protective group, e.g. an S-sulfonate ($-S-SO_3^-$) group (EP 0 037 255). A process for obtaining proinsulin having correctly linked cysteine bridges is also known (Biochemistry, 60, (1968), pages 622 to 629), which starts from proinsulin obtained from porcine pancreas, in which the cysteine residues are present as thiol residues (—SH). The term "correctly linked cystine bridges" is understood as meaning the disulfide bridges which occur in biologically active insulin from mammals.

Genetic engineering processes enable human proinsulin or proinsulin which has an amino acid sequence and/or amino acid chain length differing from human insulin to be prepared in microorganisms. The proinsulins prepared from *Escherichia coli* cells modified by genetic engineering do not have any correctly linked cystine bridges. A process for obtaining human insulin using *E. coli* (EP 0 055 945) is based on the following process steps:

Fermentation of the microorganisms—cell disruption—isolation of the fusion protein—cyanogen bromide cleavage of the fusion protein—isolation of the cleavage product containing the proinsulin sequence—protection of the cysteine residues of proinsulin by S-sulfonate groups—formation of the correctly linked cystine bridges—sulfitolysis—desalting of the proinsulin—chromatographic purification of the proinsulin containing correctly linked cystine bridges—concentration of the proinsulin solution—chromatographic purification of the concentrated proinsulin solution—enzymatic cleavage of the proinsulin to obtain human insulin—chromatographic purification of the resulting human insulin.

The disadvantages of this process are the number of process steps and the losses in the purification steps, which lead to a low yield of insulin. Because of the multi-stage process path, serious losses have to be expected. From the stage of the isolated fusion protein, an up to 40% loss of proinsulin must be expected through cyanogen bromide cleavage, sulfitolysis and purification of the proinsulin (EP 0 055 945). Similarly high losses can occur in the course of the following purification steps up to the final product.

Yield increases in the preparation of human insulin or insulin derivatives by genetic engineering can be achieved if the number of process steps necessary can be substantially decreased.

The object of the present invention was to develop a process for obtaining insulin having correctly linked cystine bridges in the insulin amino acid chain, in which fewer process steps are necessary and, all in all, lower purification losses occur.

A process for obtaining insulin of the formula I

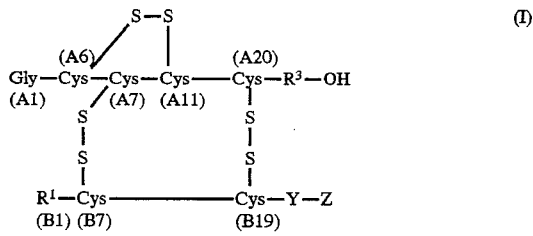

has now been found, which comprises

A) reacting a protein of the formula II (SEQ ID NO:1)

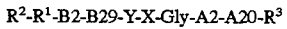

$$R^2-R^1-B2-B29-Y-X-Gly-A2-A20-R^3 \quad \text{(II)}$$

with an amount of a mercaptan which yields 2 to 10 —SH radicals of the mercaptan per cysteine residue of the protein of the formula II, in the presence of at least one chaotropic auxiliary in an aqueous medium at a pH of 10 to 11 and a concentration of the protein of the formula II of 0.05 to 0.3 g per liter of aqueous medium and B) reacting the resulting proinsulin having correctly linked cystine bridges with trypsin, a trypsin-like enzyme and optionally additionally with carboxypeptidase B or a mixture of the enzymes mentioned to give the insulin of the formula I having correctly linked cystine bridges, C) treating the reaction product thus obtained with 3 to 50 g of a hydrophobic adsorber resin per liter of aqueous medium at a pH of 4 to 7, D) isolating the adsorber resin containing adsorbed insulin of the formula I and E) desorbing the insulin of the formula I from the adsorber resin;

in this case, in formulae I and II

X is
a) an amino acid residue from the group consisting of Lys and Arg or
b) a peptide having 2 to 35 amino acid residues, containing the amino acid residue Arg or Lys at the N-terminal and carboxyl end of the peptide, Y is a genetically encodable amino acid residue, Z is
a) an amino acid residue from the group consisting of Arg and Lys,
b) a peptide having 2 or 3 amino acid residues, containing the amino acid residue Arg or Lys at the carboxyl end of the peptide or
c) OH, $R^1$ is a phenylalanine residue or a covalent bond, $R^2$ is
a) a hydrogen atom, b) an amino acid residue from the group consisting of Lys and Arg or c) a peptide having 2 to 45 amino acid residues, containing the amino acid residue Lys or Arg at the carboxyl end of the peptide, $R^3$ is a genetically encodable amino acid residue and the residues A2–A20 correspond to the amino acid sequence of the A chain of human insulin, animal insulin or an insulin derivative and the residues, B2–B29 correspond to the amino acid sequence of the B chain of human insulin, animal insulin or an insulin derivative.

A protein of the formula II (SEQ ID NO:2) is preferably employed; in this case

X is the amino acid residue Arg or a peptide having the amino acid sequence of the C chain of human insulin, Y is an amino acid residue from the group consisting of Ala, Thr and Ser, $R^1$ is the amino acid residue Phe, $R^2$ is a) a hydrogen atom or b) a peptide having 2 to 25 amino acid residues, containing Arg at the carboxyl end of the peptide, $R^3$ is an amino acid residue from the group consisting of Asn, Ser and Gly, and the residues A2–A20 and B2–B29 correspond to the amino acid sequence of the B and A chains of human insulin and an insulin of the formula I having correctly linked cystine bridges results, in this case Y, $R^1$, $R^2$, $R^3$, A2–A20 and B2–B29 have the abovementioned definition and Z is the amino acid residue Arg, the peptide residue Arg—Arg or OH.

A protein of the formula (SEQ ID NO:3) is particularly preferably employed in this case X is the amino acid residue Arg or a peptide having 2 to 35 amino acid residues, two basic amino acid residues, in particular Arg and/or Lys, being at the start and end of the peptide, Y is the amino acid residue Thr, $R^1$ is the amino acid residue Phe, $R^2$ is a) a hydrogen atom or b) a peptide having 2 to 15 amino acid residues, at whose carboxyl end is the amino acid residue Arg, $R^3$ is the amino acid residue Gly or Asn, and the residues A2–A20 and B2–B29 correspond to the amino acid sequence of the A and B chains of human insulin and an insulin of the formula I having correctly linked cystine bridges is formed, in this case Y, $R^1$, $R^2$, $R^3$, A2–A20 and B2–B29 have the abovementioned definition and Z is the amino acid residue Arg, the peptide residue Arg—Arg or Lys—Lys or OH.

Surprisingly, it has been found that the protein of the formula II does not have to be completely reduced in a reaction step customarily preceding the "refolding" (R. Jaenicke, R. Rudolph, 1989, Folding Proteins, in Protein Structure, a practical Approach; Ed. Creighton, T. E., pages 191–224, JRL Press Oxford; EP 0 219 874) and that, in the procedure described, in spite of a high proportion of foreign protein (50–90%) folding yields are achieved which are at a level comparable with the folding of appropriately purified proinsulin containing —SH protective groups.

It has further surprisingly been found that the enzymatic reaction of correctly folded proinsulin to give the insulin of the formula I having correctly linked cystine bridges is also possible in high yield in the presence of 50 to 90% of foreign protein and the insulin of the formula I binds with good selectivity to a hydrophobic adsorber resin.

Compared with the previously known methods, the process according to the invention enables substantially more rapid preparation with higher yields. The reason for this is the avoidance of the sulfitolysis and optionally cyanogen bromide cleavage process steps and the previously unknown possibility of converting proinsulin directly from its denatured state in the presence of limited amounts of chaotropic salts in high yields into a proinsulin having correctly bonded cystine bridges and then of converting it enzymatically into the insulin of the formula I without further purification. It is thereby possible to separate the resulting insulin of the formula I from the folding solution by adsorption. The insulins of the formula I can thus be obtained from the adsorbent without intermediate isolation or purification after desorption. The process according to the invention leads to a substantially shortened preparation, which because of shorter standing times and the avoidance of losses makes possible yield increases of 25–100% compared with the known processes.

The amino acid sequence of peptides and proteins is designated from the N-terminal end of the amino acid chain. The information given in parentheses in formula I, e.g. A6, A20, B1, B7 or B19, corresponds to the position of amino acid residues in the A or B chains of the insulin.

The amino acids Gly, Ala, Set, Thr, Val, Leu, Ile, Asp, Ash, Glu, Gln, Cys, Met, Arg, Lye, His, Tyr, Phe, Trp, Pro and selenocysteine stand for the term "genetically encodable amino acid radical".

The terms "residues A2–A20" and "residues B2–B29" of animal insulin are understood as meaning, for example, the amino acid sequences of insulin from cattle, pigs or hens. The term radicals A2–A20 and B2–B29 of insulin derivatives stands for the corresponding amino acid sequences of human insulin which are formed by the replacement of amino acids by other genetically encodable amino acids.

The residue Z is always part of the amino acid sequence of X and is formed by the activity of the proteases such as trypsin, trypsin-like enzymes or carboxypeptidase B. The residue $R^3$ is the amino acid residue which is in position A21 of the A chain of insulin. The residue Y is the amino acid residue which is in position B30 of the B chain of insulin.

Trypsin or trypsin-like enzymes are proteases which cleave amino acid chains at the arginine or lysine residue.

Carboxypeptidase B is an exoprotease which splits off basic amino acid residues such as Arg or Lys which are at the carboxy-terminal end of amino acid chains. (Kemmler et al., J. Biol. Chem. 246, pages 6786–6791).

The A chain of human insulin has the following sequence (SEQ ID NO:4): Gly, Ile, Val, Glu, Gln, Cys, Cys, Thr, Ser, Ile, Cys, Ser, Leu, Tyr, Gln, Leu, Glu, Asn, Tyr, Cys, Asn.

The B chain of human insulin has the following sequence (SEQ ID NO:5): Phe, Val, Asn, Gln, His, Leu, Cys, Gly, Ser, His, Leu, Val, Glu, Ala, Leu, Tyr, Leu, Val, Cys, Gly, Glu, Arg, Gly, Phe, Phe, Tyr, Thr, Pro, Lys, Thr.

The C chain of human insulin has the following sequence (SEQ ID NO:6): Arg, Arg, Glu, Ala, Glu, Asp, Leu, Gln, Val, Gly, Gln, Val, Glu, Leu, Gly, Gly, Gly, Pro, Gly, Ala, Gly, Ser, Leu, Gln, Pro, Leu, Ala, Leu, Glu, Gly, Ser, Leu, Gln, Lys, Arg.

Chaotropic auxiliaries are compounds which, in aqueous solution, break hydrogen bonds, for example ammonium sulfate, guanidine hydrochloride, ethylene carbonate, thiocyanate, dimethyl sulfoxide and urea.

The term hydrophobic adsorber resin stands for nonionic, hydrophobic, crosslinked polymers and/or copolymers, for example polyacrylates or polystyrene or copolymers of styrene and divinylbenzene, in particular polymeric adsorber resins having a large surface area and many large pores, e.g. commercial preparations of the companies Rohm and Haas or Mitsubishi Chemical Industries Ltd. such as XAD16, XAD1600 or HP20.

The term mercaptan is understood as meaning compounds which contain at least one —SH group. Water-soluble mercaptans are preferred. Examples of these compounds are dithiothreitol, dithioerythritol, 2-mercaptoethanol, cysteine, glutathione, methyl thioglycolate, 3-mercapto-1,2-propanediol and 3-mercaptopropionic acid.

The protein of the formula II (SEQ ID NO:1, 2 or 3) can be formed in microorganisms with the aid of a multiplicity of genetic engineering constructs (EP 0 489 780, EP 0 347 781, EP 0 453 969). The genetic engineering constructs are expressed in microorganisms such as *Escherichia coli* or Streptomycetes during fermentation. The proteins formed are stored in the interior of the microorganisms (EP 0 489 780) or excreted into the fermentation solution.

For the process according to the invention, proteins of the formula II (SEQ ID NO:1, 2 or 3) can be employed which are still contaminated directly after cell disruption with a multiplicity of proteins which originate from the fermentation solution and from the microorganisms. The proteins of the formula II, however, can also be employed in prepurified form, for example after precipitation or chromatographic purification.

The procedure in process step A) is as follows: The proteins are dissolved in a chaotropic auxiliary or in mixtures of various chaotropic auxiliaries. Preferably, urea or guanidine hydrochloride is used in a concentration of 6 to 9M, preferably 8M, based on water as a solvent. The pH of the reaction mixture is 8.5 to 10.8. Examples of buffers which can be used are phosphate, tri(hydroxymethyl) aminomethane (tris), borate or glycine buffer. The concentration of the buffer substances in the aqueous medium is up to 0.5M, preferably from 0.005M to 0.5M, particularly preferably from 0.05 to 0.1M. The protein mixture is then mixed with an aqueous mercaptan solution. By this means, the following concentrations are established in the reaction solution (based on water):

The concentration of the protein of the formula II (SEQ ID NO :1,2 or 3) is 0.05 to 0.6 g/l, preferably 0.1 to 0.3 g/l. The amount of the mercaptan is 2 to 10 —SH residues of the mercaptan per cysteine residue of the protein of the formula II(SEQ ID NO:1, 2 or 3), preferably 6 to 9. The pH of the solution is 10 to 11, preferably 10.8. The abovementioned buffer components are used. The exact pH is established by addition of sodium hydroxide solution. The concentration of the buffer components is 0.005 to 0.5M, preferably 0.05 to 0.1M.

The concentration of the chaotropic auxiliary in the reaction mixture containing the mercaptan is less than 1M, preferably 0.1 to 0.8M in particular 0.3 to 0.6M. The mercaptan employed is preferably cysteine or 2-mercaptoethanol, alone or as a mixture.

The temperature during the folding in process step A) is 0° C. to 50° C., preferably 2° C. to 30° C., in particular 4° C. to 10° C. The reaction time is 3 to 12 hours, preferably 4 to 8 hours, in particular 5 hours.

The result of process step A) is a proinsulin which contains correctly linked cystine bridges.

In process step B), the reaction solution from process step A) is adjusted to a pH of 6.5 to 9, preferably 8 to 9. Trypsin or a trypsin-like enzyme is added thereto in an amount from 1 to 3 mg based on 3 g of proinsulin having correctly linked cystine bridges. Optionally, carboxypeptidase B is added thereto in an amount of 3 to 8 units based on 1 g of insulin of the formula I. A mixture of trypsin and carboxypeptidase B can also be added. The solution obtained is then stirred at a temperature of 4° C. to 15° C. for from 4 to 16 hours. The result of process step B) is an insulin of the formula I which contains correctly linked cystine bridges.

In process step C), the reaction solution from process step B) is adjusted to a pH of 2.5 to 4.5 with an acid such as hydrochloric acid or sulfuric acid. If turbidity of the solution should occur, this is optionally removed by filtration or centrifugation. The remaining solution is treated with a hydrophobic adsorber resin. Resins of the XAD or HP20 type have proven suitable. The amount of the resin is 3 to 50 g per liter of reaction solution, preferably 20 to 40 g/l.

The suspension obtained can be treated with a salt such as NaCl up to a concentration of 0.1M, and is then stirred for 3 to 4 hours. The adsorption of the insulin of the formula I on the resin is checked by sampling and high-pressure liquid chromatographic analysis (HPLC analysis). As soon as insulin is no longer detectable in the solution, the adsorber resin is separated off from the aqueous reaction solution (process step D). This is carried out, for example, by filtration or centrifugation according to known methods. The resin containing adsorbed insulin of the formula I is washed with a purely aqueous or buffer-containing aqueous solution. In particular, it is washed until the conductivity in the wash solution is less than 0.4 mS/cm.

The desorption (process step E) of the insulin of the formula I is carried out by known methods, which depend on the hydrophobic adsorber resin used. The desorption is carried out in the case of XAD or HP20 adsorber resins, for example, by means of an aqueous solution which contains 20 to 65% of a water-miscible, nonionic organic solvent, e.g. a $(C_1-C_6)$-alkanol. Preferably, 35% of isopropanol or n-propanol is used in the solvent water. The desorption of the insulin of the formula I is carried out, for example, by washing with the isopropanol solution. The washing can be carried out on a stirred pressure filter by mixing with the isopropanol solution or by chromatography in a column. The volume ratio of resin to isopropanol solution is 1:1 to 1:10, preferably 1:1.1 to 1:2. The washing steps can be repeated one to five times, preferably twice. The combined isopropanol fractions can be used directly or after dilution with water for further chromatographic purifications.

In the following examples the process according to the invention is described in detail. Percentage data relate to the weight, if not stated otherwise.

EXAMPLE 1

A fusion protein having the following amino acid sequence is prepared by fermentation of genetically modified *Escherichia coil* cells (EP 0 489 780).

Proinsulin Sequence 1 (SEQ ID NO:7):

Met Ala Thr Thr Set Thr Gly Asn Set Ala Arg Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Set Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Gly

Proinsulin sequence 1 (SEQ ID NO:7) corresponds to the formula II, in this case

X is a C peptide from human insulin,
Y is Thr (B30),
$R^1$ is Phe (B1),
$R^2$ is a peptide having 11 amino acid residues,
$R^3$ is Gly (A21) and A2–A20 is the amino acid sequence of the A chain of human insulin (amino acid residues 2 to 20) and B2–B29 is the amino acid sequence of the B chain of human insulin (amino acid residues 2 to 29).

The expressed fusion protein having the proinsulin sequence 1 (SEQ ID NO:7) collects in the *E. coli* cells and forms inclusion bodies. After completion of the fermentation, the cells are removed by centrifugation and disrupted by customary high-pressure homogenization. The fusion protein inclusion bodies released are isolated by centrifugation. 2600 g of the isolated fusion protein inclusion bodies (based on dry matter after freeze drying) having the proinsulin sequence 1 (SEQ ID NO:7) are dissolved in 200 l of an 8M guanidine hydrochloride solution at pH 10.8. Optionally, after centrifugation of small amounts of suspended matter, the clear solution is stirred into 1800 l of an aqueous cysteine solution (250 g of cysteine hydrochloride hydrate) at a pH of 10.8 and a temperature of 4° C. The proportion of the insulin-containing fusion protein is determined with the aid of an SDS electrophoresis scan (U.K. Lämmli, Nature, Volume 227, pages 680–685, 1970). It is 45%. After conclusion of the folding reaction, the content of proinsulin sequence I (SEQ ID NO: having correctly linked cystine bridges in the reaction mixture is determined as 760 g with the aid of analytical HPLC.

The 2000 l of solution is adjusted to a pH of 8.5 using 6N HCl. 500 mg of trypsin is then added. 305 g of insulin 2 are formed according to HPLC measurement. Insulin 2 corresponds to the formula I, in this case Y is Thr (B30),
Z is Arg—Arg,
R$^1$ is Phe (B1),
R$^3$ is Gly (A21) and
A2–A20 is the amino acid sequence of the A chain of human insulin (amino acid residues 2 to 20) and B2–B29 is the amino acid sequence of the B chain of human insulin (amino acid residues 2 to 29).

Insulin 2 consists of the (SEQ ID NO:9) and 12, which are linked to one another via correctly bonded cystine bridges.

The solution is adjusted to a pH of 3.5 using 6N HCl and the conductivity value is adjusted to about 10 mS/cm with the aid of saturated NaCl solution. A slight turbidity is removed by centrifugation. 75 kg of HP20 (Mitsubishi Chemical Industries Ltd., Düsseldorf, Germany) are added to the clear solution. The suspension is slowly stirred at 4° C. for about 16 hours until insulin 2 (SEQ ID NO:9 and 12) is no longer to be detected in the supernatant. The resin is removed by filtration through a suction filter and washed with water until the conductivity in the wash solution is less than 0.4 mS/cm. The product is desorbed by suspension of the resin in 75 l of 50% strength aqueous isopropanol solution. Filtration and incubation with the isopropanol solution is repeated twice. After 60 minutes, the resin is filtered and then incubated several times in a 35% strength isopropanol solution and filtered. The yield of insulin 2 (SEQ ID NO:9 and 12) is 288 g.

The eluates which contain insulin 2 (SEQ ID NO:9 and 12) can be further purified immediately on a chromatography column after dilution with water and pH adjustment.

HPLC Analysis 0.5 g of protein are dissolved in 40 ml of a solution of 6M guanidine hydrochloride, 50 mM tris, pH 8.5, 5 mM ethylenediaminetetraacetate (EDTA), 1% 2-mercaptoethanol and 10 mM dithiothreitol at 95° C. for 2 min and then centrifuged at 14000 g for 20 min. 0.02 ml of the clear supernatant is applied to a high-pressure liquid chromatography column.

| Column: | NUCLEOGEL ® RP 300-5/46 (Macherey & Nagel, Aachen, Germany) |
|---|---|
| Gradient: | Buffer A: 0.1% trifluoroacetic acid (TFA) |
| | Buffer B: 0.09% TFA in acetonitrile |
| Temperature: | 55° C. |

Total running time: 40 min.
The gradient is characterized by the following amounts of buffer B after the corresponding running times:
10 min 25%, 12 min 60%, 13 min 90%, 15 min 100%.

| Flow rate: | 1 ml/min |
|---|---|
| Detection: | 215 nm |
| Retention time of insulin: | about 19 min |

EXAMPLE 2

A fusion protein having the following amino acid sequence is prepared by fermentation of a genetically modified *E. coli* (EP 0 347 781):

Fusion Protein 3 (SEQ ID NO:8)

Met Ala Pro Thr Ser Ser Ser Thr Lys Lys Thr Gln Leu Gln
Leu Glu His Leu Leu Leu Asp Leu Gln Met Ile Leu Asn
Gly Ile Asn Asn Tyr Lys Asn Pro Lys Leu Thr Arg Met
Ile Glu Gly Arg Phe Val Asn Gln His Leu Cys Gly Ser
His Leu Val Glu Ala Leu Tyr Leu Val Cys Gly Glu Arg
Gly Phe Phe Tyr Thr Pro Lys Thr Arg Gly Ile Val Glu
Gln Cys Cys Thr Set Ile Cys Set Leu Tyr Gln Leu Glu
Asn Tyr Cys Asn

This fusion protein (SEQ ID NO:8) contains the amino acid sequence of proinsulin 3 (SEQ ID NO:11). The expressed fusion protein 3 (SEQ ID NO:8) collects in the *E. coli* cells and forms inclusion bodies. The disruption of the cells is carried out as in Example 1. The fusion proteins 3 (SEQ ID NO:8) thus obtained are subjected to cyanogen bromide cleavage, and proinsulin 3 is formed (SEQ ID NO:11).

Proinsulin 3 (SEQ ID NO:11) corresponds to the formula II, in this case

X is Arg
Y is Thr (B30),
R$^1$ is Phe (B1),
R$^2$ is a peptide having 4 amino acid residues,
R$^3$ is Asn (A21) and
A2–A20 and B2–B29 correspond to the amino acid sequence of the A and B chains of human insulin.

After cyanogen bromide cleavage, the content of proinsulin 3 (SEQ ID NO:11) is determined quantitatively with the aid of SDS electrophoresis in a freeze-dried sample containing 9.2% insulin-containing protein. 2000 g of proinsulin 3 (SEQ ID NO:11) are incubated with cysteine hydrochloride hydrate as, in Example 1. A content of 1260 g of proinsulin 3 (SEQ ID NO:11) having correctly linked cystine bridges is then determined in the total reaction mixture by means of analytical HPLC. The product is treated with 500 mg of trypsin as in Example 1.

Insulin 4 is formed. Insulin 4 corresponds to the formula I, in this case

Y is Thr (B30),
Z is Arg,
R$^1$ is Phe (B1)
R$^3$ is Asn (A21) and
A2–A20 and B2–B29 correspond to the amino acid sequence of the A and B chains of human insulin. Insulin 4 consists of the, (SEQ ID NO:4 and 10), which are linked to one another by correctly bonded cystine bridges. The resulting solution (2 m$^3$) contains 800 g of the insulin derivative and is treated with 75 kg of HP20 as in Example 1. After adsorption and desorption, the combined eluate contains 703 g of insulin 4 (88% yield).

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is a hydrogen atom, an amino acid residue from the group consisting of Lys and Arg or a peptide having 2 to 45 amino acid residues, containing the amino acid residue Lys or Arg at the carboxyl end of the peptide."

( i x ) FEATURE:
        ( A ) NAME/KEY: Peptide
        ( B ) LOCATION: 2
        ( D ) OTHER INFORMATION: /note= "Xaa is a phenylalanine residue or a covalent bond."

( i x ) FEATURE:
        ( A ) NAME/KEY: Peptide
        ( B ) LOCATION: 3..4
        ( D ) OTHER INFORMATION: /note= "Xaa is the residues B2-B29 which correspond to the amino acid sequence of the B chain of human insulin, animal insulin or an insulin derivative."

( i x ) FEATURE:
        ( A ) NAME/KEY: Peptide
        ( B ) LOCATION: 5
        ( D ) OTHER INFORMATION: /note= "Xaa is a genetically encodable amino acid residue."

( i x ) FEATURE:
        ( A ) NAME/KEY: Peptide
        ( B ) LOCATION: 6
        ( D ) OTHER INFORMATION: /note= "Xaa is an amino acid residue from the group consisting of Lys and Arg or a peptide having 2 to 35 amino acid residues, containg the amino acid residue Arg or Lys at the N-terminal and carboxylic end of the peptide."

( i x ) FEATURE:
        ( A ) NAME/KEY: Peptide
        ( B ) LOCATION: 8..9
        ( D ) OTHER INFORMATION: /note= "Xaa is the residues A2-A20 which correspond to the amino acid sequence of the A chain of human insulin, aminal insulin or an insulin derivative."

( i x ) FEATURE:
        ( A ) NAME/KEY: Peptide
        ( B ) LOCATION: 10
        ( C ) OTHER INFORMATION: /note= "Xaa is a genetically encodable amino"

( x i ) SEQUENCE DESCRIPTION: SEQ ID NO:1:

```
Xaa  Xaa  Xaa  Xaa  Xaa  Xaa  Gly  Xaa  Xaa  Xaa
 1                  5                       10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is a hydrogen atom or a
            peptide have 2 to 25 amino acid residues,
            containing Arg at the carboxyl end of the peptide."

( i x ) FEATURE:
        ( A ) NAME/KEY: Peptide
        ( B ) LOCATION: 3..4
        ( D ) OTHER INFORMATION: /note= "Xaa are the residues B2-B29
            which correspond to the amino acid sequence of the B chain
            of human insulin and an insulin of the formula I having
            correctly linked cystine bridges results, in the case Y,
            R1, R2, R3, A2-A20 and B2-B29 have the abovementioned
            definition."

( i x ) FEATURE:
        ( A ) NAME/KEY: Peptide
        ( B ) LOCATION: 5
        ( D ) OTHER INFORMATION: /note= "Xaa is an amino acid residue
            from the group consisting of Ala, Thr and Ser."

( i x ) FEATURE:
        ( A ) NAME/KEY: Peptide
        ( B ) LOCATION: 6
        ( D ) OTHER INFORMATION: /note= "Xaa is the amino acid residue
            Arg or a peptide having the amino acid sequence of
            the C chain of human insulin."

( i x ) FEATURE:
        ( A ) NAME/KEY: Peptide
        ( B ) LOCATION: 8..9
        ( D ) OTHER INFORMATION: /note= "Xaa are the residues A2-A20
            which correspond to the amino acid sequence of the A chain
            of human insulin and an insulin of the formula I having
            correctly linked cystine bridges results, in the case Y,
            R1, R2, R3, A2-A20 and B2-B29 have the abovementioned
            definition."

( i x ) FEATURE:
        ( A ) NAME/KEY: Peptide
        ( B ) LOCATION: 10
        ( D ) OTHER INFORMATION: /note= "Xaa is an amino acid residue
            from the group consisting of Asn, Ser and Gly."

( x i ) SEQUENCE DESCRIPTION: SEQ ID NO:2:

Xaa  Phe  Xaa  Xaa  Tyr  Xaa  Gly  Xaa  Xaa  Xaa
1                          5                              10

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is a hydrogen atom or a
            peptide having 2 to 15 amino acid residues, at
            whose carboxyl end is the amino acid residue Arg."

( i x ) FEATURE:
- ( A ) NAME/KEY: Peptide
- ( B ) LOCATION: 3..4
- ( D ) OTHER INFORMATION: /note= "Xaa is the residues B2-B29 corresponding to the amino acid sequence of the B chain of human insulin and an insulin of the formula I having correctly linked cystine bridges is formed, in the case Y, R1, R2, R3, A2-A20 and B2-B29 have the abovementioned definition."

( i x ) FEATURE:
- ( A ) NAME/KEY: Peptide
- ( B ) LOCATION: 6
- ( D ) OTHER INFORMATION: /note= "Xaa is the amino acid residue Arg or a peptide having 2 to 35 amino acid residues, two basic amino acid residues, in particular Arg and/or Lys, being at the start and end of the peptide."

( i x ) FEATURE:
- ( A ) NAME/KEY: Peptide
- ( B ) LOCATION: 8..9
- ( D ) OTHER INFORMATION: /note= "Xaa is the resideus A2-A20 corresponding to the amino acid sequence of the A chain of human insulin and an insulin of the formula I having correctly linked cystine bridges is formed, in the case Y, R1, R2, R3, A2-A20 and B2-B29 have the abovementioned definition."

( i x ) FEATURE:
- ( A ) NAME/KEY: Peptide
- ( B ) LOCATION: 10
- ( D ) OTHER INFORMATION: /note= "Xaa is the amino acid residue Gly or Asn."

( x i ) SEQUENCE DESCRIPTION: SEQ ID NO:3:

```
Xaa Phe Xaa Xaa Thr Xaa Gly Xaa Xaa Xaa
1               5                   10
```

( 2 ) INFORMATION FOR SEQ ID NO:4:

- ( i ) SEQUENCE CHARACTERISTICS:
  - ( A ) LENGTH: 21 amino acids
  - ( B ) TYPE: amino acid
  - ( C ) STRANDEDNESS: single
  - ( D ) TOPOLOGY: linear

- ( i i ) MOLECULE TYPE: peptide

- ( x i ) SEQUENCE DESCRIPTION: SEQ ID NO:4:

```
Gly Ile Val Glu Gln Cys Cys Thr Ser Ile Cys Ser Leu Tyr Gln Leu
1               5                   10                  15
Glu Asn Tyr Cys Asn
            20
```

( 2 ) INFORMATION FOR SEQ ID NO:5:

- ( i ) SEQUENCE CHARACTERISTICS:
  - ( A ) LENGTH: 30 amino acids
  - ( B ) TYPE: amino acid
  - ( C ) STRANDEDNESS: single
  - ( D ) TOPOLOGY: linear

- ( i i ) MOLECULE TYPE: peptide

- ( x i ) SEQUENCE DESCRIPTION: SEQ ID NO:5:

```
Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Thr
            20                  25                  30
```

( 2 ) INFORMATION FOR SEQ ID NO:6:

( i ) SEQUENCE CHARACTERISTICS:
 ( A ) LENGTH: 35 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:6:

| Arg | Arg | Glu | Ala | Glu | Asp | Leu | Gln | Val | Gly | Gln | Val | Glu | Leu | Gly | Gly |
|---|---|---|---|---|---|---|---|---|---|---|---|---|---|---|---|
| 1 | | | | 5 | | | | | 10 | | | | | 15 | |
| Gly | Pro | Gly | Ala | Gly | Ser | Leu | Gln | Pro | Leu | Ala | Leu | Glu | Gly | Ser | Leu |
| | | | 20 | | | | | 25 | | | | | 30 | | |
| Gln | Lys | Arg | | | | | | | | | | | | | |
| | | 35 | | | | | | | | | | | | | |

( 2 ) INFORMATION FOR SEQ ID NO:7:

( i ) SEQUENCE CHARACTERISTICS:
  ( A ) LENGTH: 97 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:7:

| Met | Ala | Thr | Thr | Ser | Thr | Gly | Asn | Ser | Ala | Arg | Phe | Val | Asn | Gln | His |
|---|---|---|---|---|---|---|---|---|---|---|---|---|---|---|---|
| 1 | | | | 5 | | | | | 10 | | | | | 15 | |
| Leu | Cys | Gly | Ser | His | Leu | Val | Glu | Ala | Leu | Tyr | Leu | Val | Cys | Gly | Glu |
| | | | 20 | | | | | 25 | | | | | 30 | | |
| Arg | Gly | Phe | Phe | Tyr | Thr | Pro | Lys | Thr | Arg | Arg | Glu | Ala | Glu | Asp | Leu |
| | | | 35 | | | | | 40 | | | | | 45 | | |
| Gln | Val | Gly | Gln | Val | Glu | Leu | Gly | Gly | Gly | Pro | Gly | Ala | Gly | Ser | Leu |
| | 50 | | | | | 55 | | | | | 60 | | | | |
| Gln | Pro | Leu | Ala | Leu | Glu | Gly | Ser | Leu | Gln | Lys | Arg | Gly | Ile | Val | Glu |
| 65 | | | | | 70 | | | | | 75 | | | | | 80 |
| Gln | Cys | Cys | Thr | Ser | Ile | Cys | Ser | Leu | Tyr | Gln | Leu | Glu | Asn | Tyr | Cys |
| | | | | 85 | | | | | 90 | | | | | 95 | |
| Gly | | | | | | | | | | | | | | | |

( 2 ) INFORMATION FOR SEQ ID NO:8:

( i ) SEQUENCE CHARACTERISTICS:
  ( A ) LENGTH: 96 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:8:

| Met | Ala | Pro | Thr | Ser | Ser | Ser | Thr | Lys | Lys | Thr | Gln | Leu | Gln | Leu | Glu |
|---|---|---|---|---|---|---|---|---|---|---|---|---|---|---|---|
| 1 | | | | 5 | | | | | 10 | | | | | 15 | |
| His | Leu | Leu | Leu | Asp | Leu | Gln | Met | Ile | Leu | Asn | Gly | Ile | Asn | Asn | Tyr |
| | | | 20 | | | | | 25 | | | | | 30 | | |
| Lys | Asn | Pro | Lys | Leu | Thr | Arg | Met | Ile | Glu | Gly | Arg | Phe | Val | Asn | Gln |
| | | | 35 | | | | | 40 | | | | | 45 | | |
| His | Leu | Cys | Gly | Ser | His | Leu | Val | Glu | Ala | Leu | Tyr | Leu | Val | Cys | Gly |
| | | | 50 | | | | | 55 | | | | | 60 | | |
| Glu | Arg | Gly | Phe | Phe | Tyr | Thr | Pro | Lys | Thr | Arg | Gly | Ile | Val | Glu | Gln |
| 65 | | | | | 70 | | | | | 75 | | | | | 80 |

```
Cys Cys Thr Ser Ile Cys Ser Leu Tyr Gln Leu Glu Asn Tyr Cys Asn
                85              90                  95
```

( 2 ) INFORMATION FOR SEQ ID NO:9:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Thr Arg Arg
            20              25                  30
```

( 2 ) INFORMATION FOR SEQ ID NO:10:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Thr Arg
            20              25                  30
```

( 2 ) INFORMATION FOR SEQ ID NO:11:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Ile Glu Gly Arg Phe Val Asn Gln His Leu Cys Gly Ser His Leu Val
1               5                   10                  15
Glu Ala Leu Tyr Leu Val Cys Gly Glu Arg Gly Phe Phe Tyr Thr Pro
            20              25                  30
Lys Thr Arg Gly Ile Val Glu Gln Cys Cys Thr Ser Ile Cys Ser Leu
        35              40                  45
Tyr Gln Leu Glu Asn Tyr Cys Asn
    50              55
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

-continued

```
Gly  Ile  Val  Glu  Gln  Cys  Cys  Thr  Ser  Ile  Cys  Ser  Leu  Tyr  Gln  Leu
 1              5                        10                         15

Glu  Asn  Tyr  Cys  Gly
               20
```

We claim:

1. A process for obtaining insulin of the formula I

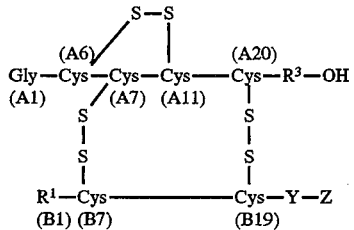

which comprises

A) reacting a protein of the formula II (SEQ ID NO:1)

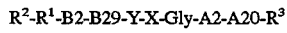

$$R^2-R^1-B2-B29-Y-X-Gly-A2-A20-R^3 \qquad (II)$$

with an amount of a mercaptan which yields 2 to 10 —SH radicals of the mercaptan per cysteine residue of the protein of the formula II, in the presence of at least one chaotropic auxiliary in an aqueous medium at a pH of 10 to 11 and a concentration of the protein of the formula II of 0.05 to 0.3 g per liter of aqueous medium and B) reacting the resulting proinsulin having correctly linked cystine bridges with trypsin or a trypsin-like enzyme and optionally additionally with carboxypeptidase B or a mixture of the enzymes mentioned to give the insulin of the formula I having correctly linked cystine bridges, C) treating the reaction product thus obtained with 3 to 50 g of a hydrophobic adsorber resin per liter of aqueous medium at a pH of 4 to 7, D) isolating the adsorber resin containing adsorbed insulin of the formula I and E) desorbing the insulin of the formula I from the adsorber resin;

in this case, in formulae I and II
X is
  a) an amino acid residue from the group consisting of Lys and Arg or
  b) a peptide having 2 to 35 amino acid residues, containing the amino acid residue Arg or Lys at the N-terminal and carboxyl end of the peptide,
Y is a genetically encodable amino acid residue,
Z is
  a) an amino acid residue from the group consisting of Lys and Arg,
  b) a peptide having 2 or 3 amino acid residues, containing the amino acid residue Arg or Lys at the carboxyl end of the peptide or
  c) OH,
$R^1$ is a phenylalanine residue or a covalent bond,
$R^2$ is
  a) a hydrogen atom,
  b) an amino acid residue from the group consisting of Lys and Arg or
  c) a peptide having 2 to 45 amino acid residues, containing the amino acid residue Arg or Lys at the carboxyl end of the peptide,
$R^3$ is a genetically encodable amino acid residue and
the residues A2–A20 correspond to the amino acid sequence of the A chain of human insulin, animal insulin or an insulin derivative and the residues B2–B29 correspond to the amino acid sequence of the B chain of human insulin, animal insulin or an insulin derivative.

2. The process as claimed in claim 1, wherein a protein of the formula II (SEQ ID NO:2) is employed, in this case
X is the amino acid residue Arg or a peptide having the amino acid sequence of the C chain of human insulin,
Y is an amino acid residue from the group consisting of Ala, Thr and Ser,
$R^1$ is the amino acid residue Phe,
$R^2$ is
  a) a hydrogen atom or
  b) a peptide having 2 to 25 amino acid residues, containing Arg at the carboxyl end of the peptide,
$R^3$ is an amino acid residue from the group consisting of Asn, Ser and Gly, and the residues A2–A20 and B2–B29 correspond to the amino acid sequence of the A and B chains of human insulin and an insulin of the formula I having correctly linked cystine bridges results, in this case Y, $R^1$, $R^2$, $R^3$, A2–A20 and B2–B29 have the abovementioned definition and
Z is the amino acid residue Arg, the peptide residue Arg—Arg or OH.

3. The process as claimed in claim 1, wherein a protein of the formula II (SEQ ID NO:3) is employed, in this case
X is the amino acid residue Arg or a peptide having 2 to 35 amino acid residues, two basic amino acid residues being at the start and end of the peptide,
Y is the amino acid residue Thr,
$R^1$ is the amino acid residue Phe,
$R^2$ is
  a) a hydrogen atom or
  b) a peptide having 2 to 15 amino acid residues, at whose carboxyl end is the amino acid residue Arg,
$R^3$ is the amino acid residue Gly or Asn, and the residues A2–A20 and B2–B29 correspond to the amino acid sequence of the A and B chains of human insulin and an insulin of the formula I having correctly linked cystine bridges is formed, in this case Y, $R^1$, $R^2$, $R^3$, A2–A20 and B2–B29 have the abovementioned definition and
Z is the amino acid residue Arg, the peptide residue Arg—Arg or Lys—Lys or OH.

4. The process as claimed in any one of claims 1 to 3, wherein cysteine or cysteine hydrochloride hydrate is employed as the mercaptan.

5. The process as claimed in any one of claims 1 to 3, wherein a crosslinked polystyrene, polyacrylate or copolymer of polystyrene and divinylbenzene is employed as the hydrophobic adsorber resin.

6. The process as claimed in any one of claims 1 to 3, wherein the insulin of the formula I is desorbed from the adsorber resin using isopropanol or n-propanol.

7. The process as claimed in any one of claims 1 to 3, wherein 0.01 to 0.1M salt is added in the process step C).

8. The process as claimed in claim 3, wherein the two basic amino acid residues at the start and end of the peptide X are Arg, Lys, or Arg and Lys.

9. The process as claimed in claim 4, wherein a crosslinked polystyrene, polyacrylate, or copolymer of polystyrene and divinylbenzene is employed as the hydrophobic adsorber resin.

10. The process as claimed in claim 8, wherein a crosslinked polystyrene polyacrylate, or copolymer of polystyrene and divinylbenzene is employed as the hydrophobic adsorber resin.

11. The process as claimed in claim 4, wherein the insulin of formula I is desorbed from the adsorber resin using isopropanol or n-propanol.

12. The process as claimed in claim 5, wherein the insulin of formula I is desorbed from the adsorber resin using isopropanol or n-propanol.

13. The process as claimed in claim 8, wherein the insulin of formula I is desorbed from the adsorber resin using isopropanol or n-propanol.

14. The process as claimed in claim 4, wherein 0.01 to 0.1M salt is added in process step C).

15. The process as claimed in claim 5, wherein 0.01 to 0.1M salt is added in process step C).

16. The process as claimed in claim 6, wherein 0.01 to 0.1M salt is added in process step C).

17. The process as claimed in claim 8, wherein 0.01 to 0.1M salt is added in process step C).

18. The process as claimed in claim 1, wherein in step B) the proinsulin is reacted with trypsin to give the insulin of the formula I having correctly linked cysteine bridges.

* * * * *

UNITED STATES PATENT AND TRADEMARK OFFICE
CERTIFICATE OF CORRECTION

PATENT NO. : 5,663,291
DATED : September 02, 1997
INVENTOR(S) : Rainer OBERMEIER et al.

It is certified that error appears in the above-indentified patent and that said Letters Patent is hereby corrected as shown below:

Claim 2, column 20, line 28, "Set" should read --Ser--.

Claim 3, column 20, line 48, "Ash" should read --Asn--.

Signed and Sealed this

Twentieth Day of January, 1998

Attest:

BRUCE LEHMAN

Attesting Officer

Commissioner of Patents and Trademarks